United States Patent
Ramos et al.

[11] Patent Number: 5,831,743
[45] Date of Patent: Nov. 3, 1998

[54] OPTICAL PROBES

[75] Inventors: Rogerio Tadeu Ramos, Cambridge, England; Edmund J. Fordham, Danbury, Conn.

[73] Assignee: Schlumberger Technology Corporation, Ridgefield, Conn.

[21] Appl. No.: 793,166

[22] PCT Filed: Jul. 31, 1995

[86] PCT No.: PCT/GB95/01792
§ 371 Date: Feb. 6, 1997
§ 102(e) Date: Feb. 6, 1997

[87] PCT Pub. No.: WO96/05499
PCT Pub. Date: Feb. 22, 1996

[30] Foreign Application Priority Data

Aug. 6, 1994 [GB] United Kingdom ............ 9415962

[51] Int. Cl.$^6$ .................. G01N 21/55; G02B 6/36
[52] U.S. Cl. ................. 356/445; 356/448; 385/85
[58] Field of Search .................. 356/445, 448, 356/120, 440, 244, 246, 73.1, 44, 409, 432, 436, 442, 133, 136, 132, 134, 135; 385/31, 38, 88, 85, 89, 133, 115, 116, 117, 120, 126, 12, 13, 15; 250/227.11, 227.2, 227.14, 227.18, 573, 577

[56] References Cited

U.S. PATENT DOCUMENTS

| | | | |
|---|---|---|---|
| 3,867,033 | 2/1975 | Hasinger | 356/103 |
| 4,320,291 | 3/1982 | Uramoto | 250/227 |
| 4,659,218 | 4/1987 | DeLasa et al. | 356/133 |
| 4,699,511 | 10/1987 | Seaver | 356/136 |
| 4,713,552 | 12/1987 | Denis et al. | 250/577 |
| 4,829,186 | 5/1989 | McLachlan et al. | 250/373 |
| 4,907,878 | 3/1990 | Arditty et al. | 356/128 |
| 5,044,723 | 9/1991 | MacDonald | 385/12 |
| 5,044,755 | 9/1991 | Landa et al. | 356/440 |
| 5,402,508 | 3/1995 | O'Rourke et al. | 385/31 |
| 5,664,036 | 9/1997 | Islam | 385/31 |

FOREIGN PATENT DOCUMENTS

| | | | |
|---|---|---|---|
| 0 194 732 A3 | 9/1986 | European Pat. Off. | G01N 21/43 |
| 0 237 850 | 9/1987 | European Pat. Off. | G01F 23/04 |
| 0 282 655 A2 | 9/1988 | European Pat. Off. | G02B 6/36 |
| 0 296 705 A2 | 12/1988 | European Pat. Off. | G01N 21/31 |
| 2 577 045 A1 | 8/1986 | France | G01N 21/41 |
| 51988 | 4/1977 | Japan | 356/133 |
| WO 91/10133 | 7/1991 | WIPO . | |

OTHER PUBLICATIONS

Vince, M.A. et al., *Optical Prove for High–Temperature Local Void Fraction Determination*, 2219 Applied Optics, vol. 21 (1982) Mar., No. 5, New York, pp. 886–892.

*Primary Examiner*—Frank G. Font
*Assistant Examiner*—Michael P. Stafira
*Attorney, Agent, or Firm*—Keith G. W. Smith; Peter Y. Lee

[57] ABSTRACT

After an oil well has been drilled, lined and cased, and is producing, it may be desirable in situ (either at the wellhead or downhole) to measure, and log (record), the rate at which fluid, and its several distinct components, is flowing out of the geological formations through which the bore has been drilled and is passing into and up the casing. A useful type of detector system for this purpose is an optical probe (31), and the invention proposes a novel design of probe which has a doubly-angled tip, there being measured the light totally internally reflected at the interface (37), which depends on the ratio of the refractive indices of the probe tip and fluid component in which it is immersed. The invention also proposes an improved method using such a tipped probe, in which, to facilitate distinguishing between the components of a multiphase fluid such as the gas/water/oil formation fluid in an oil well, there is employed a pair of adjacent probes, one of which is designed to distinguish between gas and liquid and the other of which is designed to distinguish between oil and "not oil" (gas/water), and there are then logically combined the outputs of the two so as to give an indication of which component the probes are in.

24 Claims, 7 Drawing Sheets

OPTICAL PROBES

This invention relates to optical probes, and particularly (but not exclusively) to such probes as may be useful in multiphase fluid component discrimination. The invention concerns especially probes for component discrimination and volume fraction measurement of a fluid containing multiple immiscible phases flowing along a channel, and more specifically still the invention relates to measuring the flow of the components of the gas, oil and water mixture commonly encountered in the bores of oil wells.

BACKGROUND OF THE INVENTION

Once completed, an oil well normally has a concrete-lined elongate borehole with 7 inch (17.5 cm) diameter tubular casing disposed therein. Formation fluids and treatment fluids pass through holes in the lining/casing and up/down the core of the borehole via whatever valves, sampling chambers and other mechanisms may be contained therein, either downhole or at the top of the well. One such mechanism may be a device for measuring the flow rate of the formation fluids up the borehole, for after a well has been drilled, lined and cased, and is producing, it will on occasion be desirable to measure, and log (record), the rate at which fluid is flowing out of the geological formations through which the bore has been drilled and is passing into and up the casing. While such a measurement at the wellhead will be adequate for most purposes, it may also be desirable—because this fluid will often be issuing at two or more levels from the formations through which the bore passes, and thus can have a corresponding number of compositions and flow rates—to be able to measure each in situ rather than as a combination when the fluids all reach the top of the casing as a mixture of the individual fluids. Thus, there is a need for a flow measuring device which can not only be used at the wellhead (where the flow may be a mixture of oil, brine and as much as 90% or more by volume gas) but can also be lowered as part of a production-logging or -monitoring tool string down the bore hole to a chosen depth, where there issues the fluid of interest (which may be an oil/brine/gas mixture with, typically, only a few gas bubbles because of the great ambient pressure).

As might be expected, one simple type of flow measurer is a propeller (or fan) acting as a turbine and driven round by the fluid passing "through" it. Such devices, which, coupled to a suitable generator, provide a flow-rate-dependent output signal (usually electrical in nature) that can be fed to metering equipment either included as part of the downhole measurer package or sited at the wellhead, are in use, and in many circumstances work well. However, they do have their limitations, particularly when applied to the formation fluids commonly encountered in oil wells (which are usually two- or three-phase fluids, being for the most part a mixture either of water [brine] and oil or of water, gas [mostly methane] and oil), and for various reasons it may be preferable to employ, instead or as well, one or more point device such as an optical probe, which relies for its operation on the interface properties of a fibre optic waveguide projecting into the fluid being observed.

Light travelling along a guide, such as an optical fibre, is kept within the guide by total internal reflection at the guide's boundaries provided that there is a small difference—about 1% is normally satisfactory—between the refractive index of the guide material and the refractive index of the surrounding medium. Similarly, when that light reaches the end (or tip) of the guide it may, or may not, be reflected back from the tip/medium interface (rather than exiting the guide). Whether it is or not depends upon the tip reflectivity (the reflected power ratio, which in turn depends on the refractive index contrast; whenever light travels across an interface between two materials some of it is always reflected/scattered back at that interface), and also upon the shape of the guide's end face or faces (coupled with the refractive index values, this determines whether light reaching the interface undergoes total internal reflection thereat). This effect has been employed to construct so-called optical probes that allow the detection of some external condition, such as the presence or absence of a particular material at the operational end of the probe, by seeing whether light passed down to the tip of a light guide forming the core of the probe is, or is not, reflected back. For example, if a normally-cleaved optical fibre probe—a probe with its tip cut at a rightangle to the probe axis—is placed in a container of water with its tip immersed in the water the refractive index difference (between the guide material and the water) may be sufficiently low that all, or most, of the light exits the guide, whereas if the water is removed, so the tip is in air, the refractive index contrast is large enough to cause an appreciable amount, perhaps as large as 3.5%, depending upon the guide material, of the light to be reflected back up the guide (and the difference in the amount of light reflected is easily detectable by modern equipment). By inspecting the amount of light travelling back up the guide the probe can thus be used with confidence to detect the presence or absence of water in the container.

The smaller the difference between the refractive index n of the probe material and that of the substance in which its tip is immersed the less light is reflected/scattered back from the interface. Thus, using typically a probe made of a silica glass of refractive index n=1.46, then the amount of light reflected back from the interface when it is formed with an oil—a heavy oil is likely to have an index of n=1.5, while a very light oil has n=1.42—is significantly less than that reflected back when the tip is immersed in water (n=1.33), and that reflected back when the tip is in gas (n=1) is significantly more.

This use of an optical probe has already been made in oil-in-water fluids, such as the formation fluids found in oil well boreholes, to enable not only a measurement of the composition of the fluid—and specifically of the volume fraction of the dispersed oil phase—but also, and separately, a measurement of the velocity of the dispersed phase.

In principle, these differences in reflected/scattered light can be used to provide an indication of the passage of each of the formation fluid's immiscible components past the probe, and so enable the drops, bubbles or other fluid "lumps" of these components to be discriminated and their individual flow rates to be determined. Unfortunately, in practice this simple approach has not proved reliable, and accordingly the invention proposes a novel design of probe (and a novel technique using such a probe), and suggests that, instead of there being measured the light returned from the probe/fluid interface by ordinary reflection/scattering (which is normally less than 4% of the incident optical power), as is the case resulting from the utilisation of a probe with a square-cut tip, there be employed a probe with an angled tip, and there be measured the light totally-internally reflected at the interface.

Total internal reflection is a common and well-understood phenomenon that can occur when light is shone from one medium (such as water) which is optically more dense (has a higher refractive index $n_2$) into a second medium (such as air) which is optically less dense (a lower $n_1$) at an angle to the interface between the two. As the angle—the angle θ the light beam makes with a line normal to the interface—is increased, and the light entering the less dense medium is refracted into a path closer and closer to the plane of the interface itself, there is reached a point (the critical angle, θ $_{cr}$) where the angle is such that, instead of being transmitted, the light is totally reflected at the interface back into the more dense medium, just as if the interface had become a perfect mirror. For any pair of media the critical angle θ $_{cr}$ may be determined from the equation $$\theta_{cr} = \arcsin \frac{n_1}{n_2}$$

As noted above, a proposed solution to the problems of using a square-cut probe tip to look at gas/liquid fluids is to employ a probe with an angled tip, there then being measured the light totally-internally reflected at the interface (as explained further hereinafter, this reflected light is then subjected to a second reflection which causes it to be re-directed back up the optical fibre to an appropriate detector system). This total-internal-reflection, or TIR, solution relies on the tip angle α—the angle the plane of the tip, and thus of the interface, makes with the axis of the probe—being such that light travelling down the probe's guide arrives at the tip at an angle θ to the interface normal line (θ=90°−α) which is arranged to be of a value relative to the likely range of critical angles for each probe material/fluid substance pair of interest—for instance, probe/gas or probe/liquid—that for one pair (probe/gas) there is total internal reflection while for the other (probe/liquid) there isn't. For example, for a silica glass (n=1.46) probe protruding into a fluid having both gas and water phases, the critical angle θ $_{cr}$ for use with gas (n=1) is 43.2° while the critical angle for use with water (n=1.33) is 65.6°, and for crude oils (n=1.42, say) it is 77° (if total internal reflection can occur at all). So, if the probe angle α is set such that θ is between the critical angles for gas and water—45°, say—there will be total internal reflection for a passing gas phase portion but no significant reflection for a passing liquid (water or oil) phase moiety. This provides a "yes/no" situation which makes it very easy to decide whether the probe is in gas or liquid—and thus to discriminate between the fluid's gas and liquid components—and then to determine how much of each is flowing past the probe.

Of course, to result in some useful effect the TIRed light must be sent back up the probe's optical fibre to whatever detector system is being employed, and, as intimated above, this returning of the TIRed light may be achieved by providing the probe's tip with a secondary reflector—as discussed further hereinafter this can be a corner reflector or a second simple surface—reflection at which causes the light to be sent back along the fibre. It will be necessary, to ensure near total reflection at this secondary reflector, deliberately to make its reflective surface(s) mirror-like (and ways of achieving this are discussed hereinafter).

In what follows, and throughout this Specification, it is assumed that any reference to an angle between two planes is to the angle measured in another plane normal to the first two, while any similar reference to an angle between a line and a plane is to the angle measured in another plane that both contains the line and is normal to the first plane. Moreover, the angle referred to is wherever relevant the included angle lying between the appropriate surfaces (or line and surface). In the event of confusion in any particular case, a reference to the Figures in the accompanying Drawings should clarify matters.

SUMMARY OF THE INVENTION

Figure 3A:
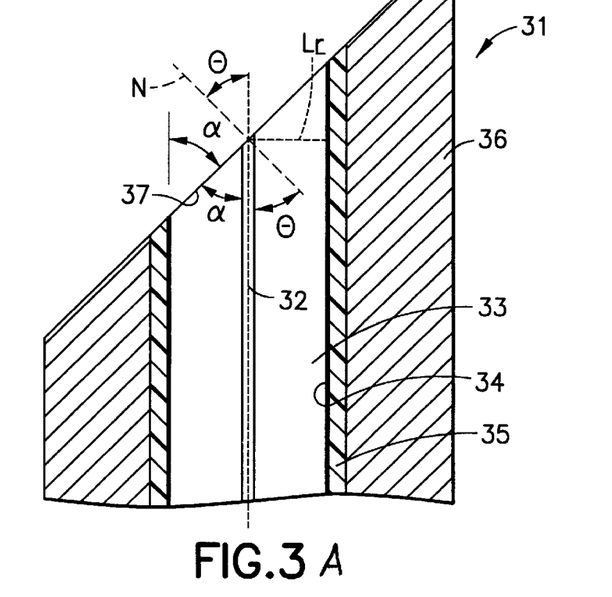
FIGS. 3A to 3G show schematically the nature of five slightly different probe tips for use in the method of the invention.
Figure 3B:
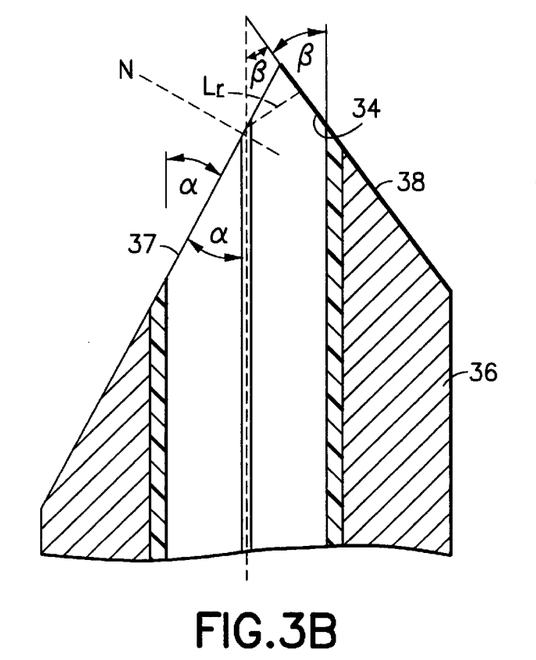
Figure 3C:
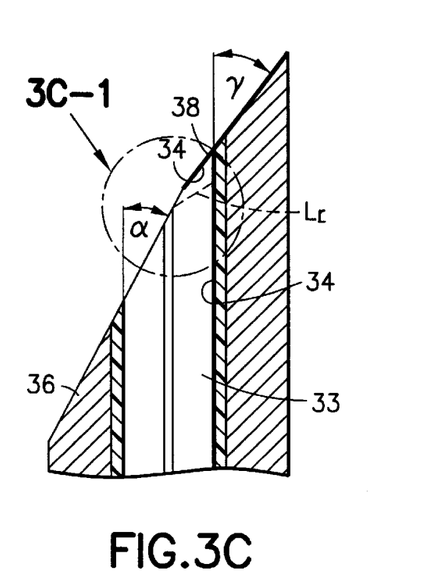
Figure 3C:
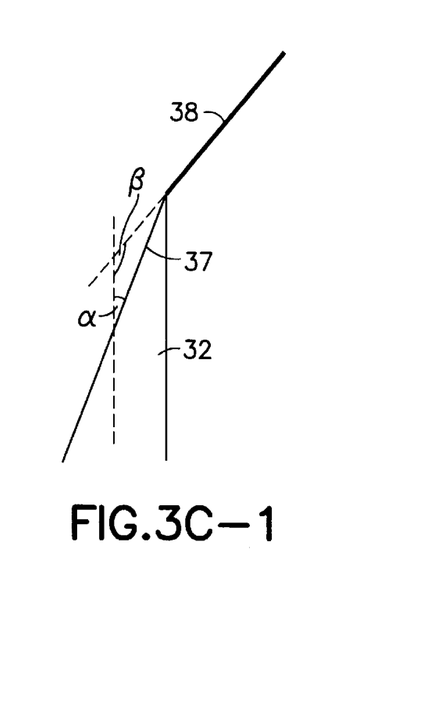
Figure 3D:
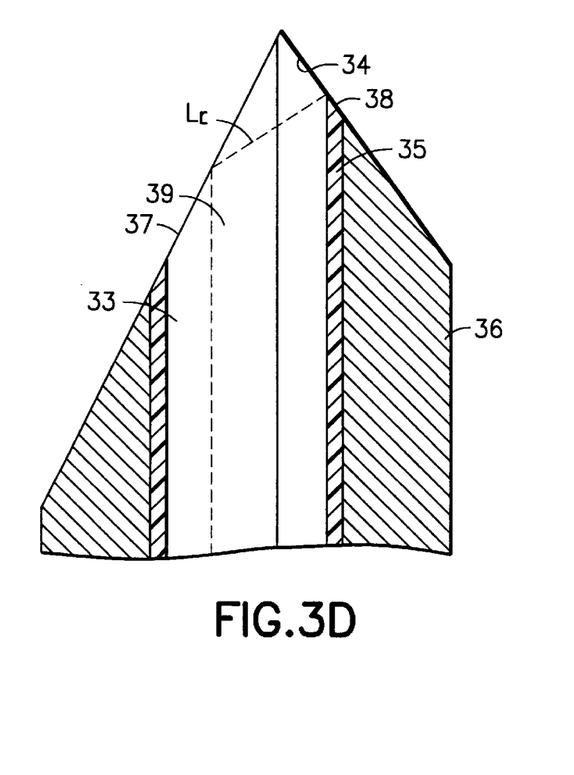
Figure 3E:
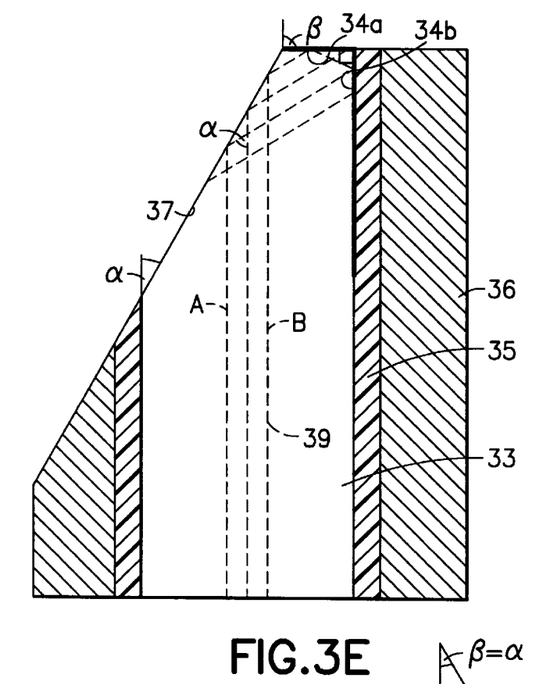
Figure 3F:
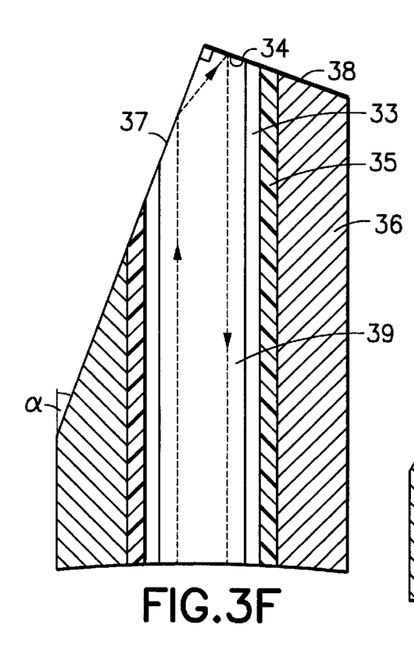

The TIRed light is reflected by the secondary reflector, and this second reflection may either send it straight back up the fibre (as is shown in FIG. 3F of the accompanying Drawings, discussed further hereinafter), or it may cause the light to re-trace its path back to the interface surface, where it again undergoes total internal reflection and then is sent back up the fibre (as shown in, for example, FIG. 3A of the accompanying Drawings). In the first case a cursory examination of the geometry of the probe tip shows that, to ensure that light TIRed at the interface is reflected at the secondary reflector back along the fibre, the secondary reflector must be substantially at rightangles to the interface. In the second case, in which the light is first reflected back to the interface by a second reflection that reverses its direction, and so sends it back along its outward path, examination of the probe tip geometry and optical characteristics shows that, to ensure that light TIRed at an interface having an angle α to the fibre axis is reflected back along its outward path, it must meet, and be reflected from, either something like a corner reflector (as in FIG. 3E of the accompanying Drawings) or a second simple surface at an angle of about 90°−α to the interface (as in FIG. 3A aforementioned). In this latter case, the exact relationship involves the refractive indices of the fibre's components; defining the angle of this second, simple reflective surface with reference to the fibre axis, it is at an angle of about 90°−2α. In either form where a simple reflective surface—not a corner reflector—is employed, the second reflection may itself be either direct or—as in FIG. 3C of the accompanying Drawings—via an intermediate surface, as is explained hereinafter.

A probe with such a tip, making it "doubly reflective", is novel and inventive. Accordingly, in a first aspect the invention provides an optical fibre probe which includes a fibre tip having a surface at an angle α to the fibre axis and another surface at an angle β to the fibre axis, the former surface providing a "fluid-sensitive" interface and the latter surface providing, or forming part of, an intrinsically highly-reflective secondary reflector, the two surfaces being either angularly or positionally asymmetrically oriented with respect to the fibre axis and being so oriented both mutually and with respect to the fibre axis that light guided along the fibre to the tip and reflected off the fluid-sensitive interface surface towards the secondary reflector is reflected back along the fibre.

As used herein the term "fluid-sensitive" as applied to one of the tip's surfaces means that the surface is one at which total internal reflection, TIR, can occur when the tip is in an appropriate fluid. This is discussed further hereinafter.

For the most part, the probe of the invention will find a use in the distinguishing of the multiple components of a multiphase fluid, and is mainly so described herein. As also discussed hereinafter, though, it does have other uses.

The probe definition given above covers two main types of probe tip. In the first, which is particularly suited to multimode wide-cored fibres wherein the guided light does not need to leave the core and pass into the cladding, the primary requirement is that the secondary reflector—conveniently a simple reflective surface—be effectively at an angle of 90° to the fluid-sensitive interface (at which TIR occurs), for that will simply reflect the TIRed light back up the core, albeit not exactly along its outward path. The second, which is suitable for both wide- and narrow-cored fibres (and the TIRed light may need to leave the core and pass into the cladding), is itself notionally divisible into two sub-types, a corner-reflector version and a simple surface version. The first of these—the corner-reflector version—is one wherein two simple reflective surfaces are brought together at rightangles, to make an internally-reflective corner (like that between a wall and a floor); the optical geometry of such an arrangement ensures that light input to the corner and striking one of the reflective surfaces is reflected towards the other, from which it is reflected in turn back along a path parallel to its input path. The two simple reflective surfaces do not need to be exactly planar—flat—although that is usually preferred; in one satisfactory embodiment one of the two surfaces is in fact the curved outer surface of the optical fibre. The second version—the simple surface version, where the probe has a tip having a "fluid-sensitive" interface at an angle $\alpha$ to the axis and a secondary reflective surface at an angle $\beta$ to the fibre axis—has the requirement that the relationship between $\alpha$ and $\beta$ should be such that $$\operatorname{Sin}\beta = \frac{n_{core}}{n_{clad}} \times \operatorname{Sin}(90^\circ - 2\alpha)$$

(wherein $n_{core}$ and $n_{clad}$ are respectively the refractive indices of the core and cladding).

A major use for the probes of this invention is in the distinguishing of the components of a multiphase fluid such as an oil well formation fluid. Accordingly, in a second aspect the invention provides a method of distinguishing between the components of a multiphase fluid, which components have significantly different refractive indices, in which method:

there is inserted into the fluid a "doubly-reflective" optical probe of the invention, the probe having a tip having a "fluid-sensitive" interface surface at an angle $\alpha$ to the axis chosen such that for the particular tip material being used the interface/normal angle $\theta$ lies between the critical angles $\theta$ crfor the phase pairs of interest;

there is measured the light returned by the probe, to give an indication of whether the probe is in a fluid component which causes total internal reflection or not; and this indication is used to denote in which fluid component the probe is disposed.

The tip of the probe of the invention is asymmetric—either because, as is preferred, the angles $\alpha$ and $\beta$ are not the same (angularly asymmetric), or because the tip's point is laced laterally to one side or the other of the probe axis (positionally asymmetric as discussed further hereinafter, in such a case the placement is advantageously away from the fluid-sensitive-surface side and towards the secondary-reflector side, for this minimises light wasted).

In its first form the invention's probe has a tip with a secondary reflective surface which is at an angle of 90° to the fluid-sensitive interface (at which TIR occurs). The angle $\alpha$ of the interface to the fibre's axis may be any required for the probe's TIR-driven component-distinguishing purpose (and, naturally, the angle $\beta$ of the secondary reflective surface to the fibre axis will be whatever corresponds—that is, 90°–$\alpha$).

In the probe's second form the TIRed light arrives at a secondary reflector which is either a corner reflector or a simple secondary reflective surface at rightangles to the path of the TIRed light, and thus is reflected back along the outward path via the interface. The corner-reflector version is particularly attractive because, other than accurately forming it (which is relatively easy), there is no pressing need accurately to orient it in any special way relative to the interface. By contrast, where a simple secondary reflective surface is utilised it is in general important that the angle $\alpha$ of the interface to the axis and the angle $\beta$ of the secondary reflective surface to the axis have the required relationship. If the geometry of the tip is such that the light necessarily has to pass into the cladding on its way to the secondary reflective surface—as will commonly be so when utilising a relatively narrow and/or single-mode fibre—then the required $\alpha$, $\beta$ relationship is that defined above involving the ratio of $n_{core}$ to $n_{clad}$. If, however, the tip geometry allows light from the core to reach the secondary reflective surface without passing into the cladding—as will commonly be the case when employing relatively wide core and/or multimode fibre—the the refractive indexes are irrlelvant, and the required relationship is $\beta = 90^\circ - 2\alpha$.

The probe of the invention has a tip having a "fluid-sensitive" interface (that is, an interface exposed in operation to the fluid, and causing total internal reflection, or not, depending upon the nature of that fluid) at an angle $\alpha$ to the axis. As will be appreciated from the explanation hereinbefore, the tip interface angle $\alpha$ is chosen to "match" whatever pair of phases is of interest—that is to say, such that for the particular tip material being used the interface/normal angle $\theta$ lies between the critical angles $\theta_{cr}$ for the phase pairs. In the case of the gas/water/oil mixture in an oil well formation fluid, for distinguishing gas from liquid using, say, a silica or sapphire probe a suitable angle $\alpha$ is within the range 25° to 45°, especially 45°, while for distinguishing between oil and "not oil" (either gas or water [brine]) an angle $\alpha$ range of 5° to 25°, especially 17° or 37° (for a silica or sapphire probe respectively) is suitable.

In the probe of the invention there is a secondary reflector (the or each reflective surface of this reflector is made mirror-like, as discussed further hereinafter, so as to reflect back substantially all the light falling on it). The interface surface itself—for convenience referred to hereinafter merely as "the interface"—is the surface notionally produced by cutting across the probe tip at the relevant angle to form a facet, while the simplest form of secondary reflector is that notionally produced by a second facet cut at the "back" of the first (in the corner reflector version it is an orthogonal pair of facets). It will be appreciated that, in the case where the probe is a simple-reflective-secondary-surface version of the second form (with a tip the secondary reflective surface of which sends the TIRed light back to the interface and then back up the fibre), then where the tip interface angle $\alpha$ is 45° the angle (with the axis) of the secondary reflection surface is 0°, making it actually parallel to the fibre axis. Indeed, in this one case the second surface can be the (curved) outer surface of the fibre itself (an example of this is discussed further hereinafter with reference to FIG. 3A of the accompanying Drawings).

In the invention's first form of probe, where the secondary reflector is a reflective surface that directs the TIRed light directly back up the fibre, the interface and the reflective surface need be at 90° to each other. Most usually the tip will have two (and only two) facets, constituting these two surfaces, and the TIRed light will be reflected from the interface directly to the secondary reflective surface. However, it is possible to conceive of a tip with three or more facets (not necessarily all plane parallel) so arranged and angled one to the next that the TIRed light is reflected off one or more intermediate reflective surface before it reaches the defined secondary reflective surface. As long as the "included" angle between the interface and the secondary reflective surface is 90°, the TIRed light will be sent by the latter back up the fibre.

In the simple-secondary-reflective-surface version of the second form of probe (as discussed hereinafter with reference to FIGS. 3A and 3B of the accompanying Drawings)

the secondary reflection surface will normally be at an acute angle to the interface, and in such an arrangement the light TIRed off the interface proceeds directly to, and is then reflected directly back from, the secondary reflection surface. In this case the equation given above linking $\alpha$ and $\beta$ can be approximated to $\beta=90°-2\alpha$. a when the two refractive indices are similar. It will be appreciated, however, that it is possible to cut the probe tip such that the secondary reflection surface is at an obtuse angle to the interface, and then to arrange that the TIRed light is first directed to, and reflected from, the exterior of the cladding, from which it is re-reflected on to the secondary reflection surface proper (and then reflected back along the fibre—possibly along the same path, via the cladding exterior, to the interface, and thence back up the fibre). In this case the equation given above linking $\alpha$ and $\beta$ can be approximated to $\beta=90°+2\alpha$ when the two refractive indices are similar. An example of such an indirect re-reflection structure is discussed hereinafter with reference to FIG. 3C of the accompanying Drawings.

The secondary reflector surface reflects the TIRed light from the interface directly or indirectly back up the fibre. As noted hereinbefore, the or each reflective surface of this secondary reflector surface (and, indeed, the exterior of the cladding) is made especially reflective to ensure that as much as possible of the TIRed light is returned. This can be achieved by giving the surface a highly reflective coating, typically of silver or some other metal, or combination of metals, such as gold, platinum, nickel, aluminium, molybdenum and/or chromium (or perhaps by employing instead a multilayer dielectric coating that provides near 100% reflection using interference effects).

As observed hereinbefore, the corner-reflector version of the second type of probe is preferred over the simple-secondary-reflective-surface version because it is easier and less demanding of accuracy to make the former. The corner-reflector version is also preferred for two other reasons; first, because of its inherently "blunt" shape it is more robust than the other, and second, it has a larger "acceptance" angle, as can be seen from its geometry, and so can accommodate variations from "geometrical" optical incidence caused by thin films of a wetting liquid, which film may not be perfectly parallel to the solid interface surface.

The invention provides a probe; in essence this probe is no more than a length of optical fibre the tip of which is specially shaped, and the term "probe" used herein includes that within its scope. However, while naturally the fibre could be used without any form of jacketing, in practice the fibre is conveniently covered with some sort of protective sheath. For instance, it could be given a polymer or brazing metal layer, the whole being mounted (perhaps with a resin adhesive) into a metal, conveniently steel, needle of some suitable external diameter with the very tip projecting therefrom. Alternatively, a thick fibre can simply be given a hard coating—of Diamond-like Carbon (DLC), say—and then used as it is.

The major use for the probes of the invention is in distinguishing the components of a multiphase fluid from each other, and particularly in the distinguishing of the components of an oil well formation fluid. The comments now following relate primarily to probes for such a use.

It will be appreciated firstly that the exposed tip of each probe may well need some protection from the physical and chemical nature of the components in the fluid under test. In an oil well formation fluid, for example, there will inevitably be a myriad of abrasive particles derived from the rock formations through which the well has been bored. The desired protection can be achieved by providing a hard, protective layer or coating on the tip, and this is discussed further below.

Secondly, it will be understood that there may be some problems in the operation of the probe, and in the interpretation of its output, if the probe tip is wet by one of the fluid's components—that is to say, if that component forms a "permanent" layer or coating on the tip (or on any protective coating on the tip)—and if the formed wetting coating or layer is of material that has a refractive index that is itself significantly different from (and specifically significantly less than) that of the optical fibre material or that of any protective coating thereon. In an oil well formation fluid, for example, the refractive index of the oil components will be around 1.5 or slightly less, which is greater than (but close to) the refractive index of 1.46 for a typical silica glass probe, so were that to be the wetting material it would not matter. However, the water component of such a fluid will have a refractive index of around 1.33, and if that were to be the wetting film it would be a serious problem. The reason for this problem is simple: if the probe is wetted by a fluid of lower refractive index than others from which that fluid should be discriminated by the probe's geometry then the thin, lower-index wetting film will cause total internal reflection even when the probe is actually immersed in the higher-index fluid. Then, because the probe is effectively always in the lower-index material, and never not in it, it will always provide the high output, and so it will be unable to distinguish between whichever "pair" of materials it was designed for. In the case of a gas/water/oil formation fluid, for example, if a silica glass probe has a tip angle designed to give a high output in gas or water (because of total internal reflection) and a low output in oil (because of no such reflection), then if wet by the water phase any light input to the probe will always be reflected at the water layer even though the tip may actually be in oil, and the probe will be unable to distinguish between gas/water and oil as it was designed to do.

It is important, then, that in the component-distinguishing method of the invention there be used probes the tips of which are either not wet by any of the fluid components likely to be encountered or, if they are wet, are wet by such a component the refractive index of which is of such a value relative to that of the probe's fibre that no total internal reflection is expected to occur when the tip is immersed in that component.

Arranging for the tip not to be wet at all may be rather difficult, whereas contriving that it be wet by an acceptable liquid is easier. Thus, it is relatively easy to provide a silica glass probe tip with a hydrophobic, and oleophilic, coating that will prevent the tip being wet by any aqueous component in the fluid and will instead ensure that any wetting that does occur is effected by an oil component. And while such a hydrophobic coating might be applied using chemical silanisation of oleophilic molecular functional groups to the surface of the silica, it transpires by chance that the preferred hard, protective coating materials, as now described, do indeed give the tip the required oleophilic, oil-wetting, nature.

As observed above, the exposed tip of each probe is likely to need some protection from the fluid under test, and this can be achieved by providing a hard, protective layer or coating on the tip. Of course, the coating must not upset the optics of the probe—it should preferably be: amorphous, so facilitating the formation of an optically flat coating; adequately transparent at the probe's operating wavelength; depositable with good thickness control (so as, in accordance with the well-known theorem, to permit the coating to be formed with a thickness equal to a whole number of half wavelengths of the light used, and by interference effects thus reduce additional reflectivity to a negligible value); and of a refractive index greater than that of the probe's fibre optic (and than that of any likely fluid component), so as not itself to cause total internal reflection of probe light. Moreover, the coating must have some fairly rigorous physical properties—it should be: extremely hard (to resist abrasion); very stiff (to protect against impact); and easily bonded to the probe tip material. And, of course, in use it should present a hydrophobic surface. Suitable materials are diamond (as polycrystalline diamond) and a number of diamond-like substances, such as Diamond-Like Carbon (known as DLC), which is also known as Amorphous Partially Hydrogenated Carbon (or a-C:H). DLC is transparent in the infra-red region, has a refractive index around 2.2, and gives smooth amorphous hydrophobic coatings. Other possible materials are the related Tetrahedral Amorphous Carbon (ta-C) and Partially Hydrogenated Tetrahedral Amorphous Carbon (ta-C:H), and variants of hard carbon films containing a proportion of silicon, as well as materials like oxides such as alumina (sapphire) or tantalum oxide ($Ta_2O_5$) which, though water-wettable, and thus not really preferred, can be made hydrophobic by the use of certain surfactants. Yet other advantageous materials are some of the corresponding partially fluorinated substances, for instance a-C:H-F, which, although still very hard, provides a surface which is Teflon-like in its wetting properties (TEFLON is a Registered Trademark). Still further useful materials are nitrides, such as aluminium and silicon nitride. In general all these materials can be used to form protective tip coatings by utilising conventional plasma or chemical vapour deposition techniques, and no more need be said about that here.

In the particular case of applying the method of the invention to a gas/water/oil oil well formation fluid using a silica glass probe the tip of which has a hydrophobic, and oleophilic, coating, so that any wetting that does occur is effected by an oil component, it is a fortunate coincidence that the refractive index of the oil—1.5 or just below—is close to that of the silica glass. The result is that the combination of glass, hard coating (of n half-wavelengths' thickness) and any oil layer behaves very much as though it were optically all the same—as though the oil wetting layer were simply an extension of the glass—and therefore the probe's output is not significantly different from what it would have been were there to have been no wetting of the tip at all. Had the wetting layer been water, this would not have been the case, and the outputs' difference would have been highly significant.

A single probe of the invention can be utilised to distinguish between more than two components—an oil well formation fluid is, as observed, usually a three-phase fluid, having gas, water and oil portions, and what is really required is the ability to distinguish not just between gas and liquid but also between water and oil. One possible way of doing this is to have a probe where the material (such as silica glass) and the tip angle $\alpha$ (=90°−$\theta$) are so chosen that for one extreme possible pair—probe/gas, critical angle $\theta_{cr}$≈43.2°—there is total internal reflection, for the other extreme possible pair—probe/light oil, critical angle $\theta_{cr}$ at least 76°—there is no such reflection, and for the intermediate pair—probe/water, critical angle $\theta_{cr}$ 65.6°—there is "partial" such reflection. For example, for a silica glass probe angled to provide a light/interface normal angle $\theta$ of just fractionally below the probe/water critical angle, such as 65.5°, the gas interface would give 100% reflection, the water interface would give an intermediate intensity (about 50%), and the oil interface would give below 1%. However, the problems of getting the probe angle $\alpha$ right, and then of correctly orienting the probe, and of coping with temperature- or salinity-derived changes in the water's refractive index (as will occasionally occur), make this way of measuring a three-phase fluid rather difficult, and it may be more suitable to use two (or more) probes one of which is designed to distinguish between gas and liquid and the other of which is designed to distinguish between gas/water and oil. These may be spaced apart, the individual outputs then being used to calculate some an average for the fluid moving past them (and the two [or more] averages may be used in a determination of how much of each of the three [or more] components there were), or they may be positioned closely adjacent, even so close as to be "looking" at essentially the same volume of fluid. Indeed, with this possibility in mind, the invention in yet further aspects seeks to deal even more effectively with the problem of determining the components of a three-phase fluid in a different, but surprisingly simple and effective, way.

More specifically, the invention proposes that the discrimination of the components of a gas/water/oil fluid preferably be carried out not using a single probe but by using at least a pair of closely-adjacent probes, one of which is designed to distinguish between gas and liquid and the other of which is designed to distinguish between gas and water on the one hand and oil on the other, and by then logically combining the outputs of the two so as to give an indication of which component the probes are in. In the example referred to above, if one probe (Probe 1) were to have an angle $\alpha$ of 45° and thus an interface/normal angle $\theta$ of 45° (=90°−45°), which is greater than the probe/gas critical angle (43.2°), then it would satisfactorily distinguish between gas (much light reflected) on the one hand and either water or oil (little light reflected) on the other, while if a second probe (Probe 2) were to have an angle $\alpha$ of 17° so that the interface/normal angle was 73° (=90°−17°), which is greater than the probe/water critical angle (65.6°), then it would satisfactorily distinguish between either gas or water (much light reflected) on the one hand and oil (little light reflected) on the other. And then, by logically combining the two sets of probe readings, it is easy to decide which phase the probes are in—if both probes have a high output the phase is gas, if Probe 1 is high but Probe 2 is low it's water, and if both probes are low it's oil. Clearly, this principle—using probes with interface/normal angles $\theta$ spread over a range corresponding to the components of the multiphase fluid being measured, and logically combining the results to indicate which phase the probes are presently in—is applicable in many areas.

In another aspect, therefore, this invention provides a method of distinguishing between the components of a multiphase fluid, which components have significantly different refractive indices, in which method:

there is inserted into the fluid a closely-spaced set of optical probes of the invention having tips "matched" to—with different interface/normal angles $\theta$, each angle $\theta$ being set between the critical angles for—a phase pair of interest;

there is measured the light returned by the probes, to give an indication of whether each probe is in a component which causes total internal reflection or not;

and these binary indications are logically combined to indicate in which component the probes are disposed.

There can, of course, be two, three, four or more probes, depending on the number of phase pairs that are of interest.

However, the invention is of particular value in the determination of the composition of the mainly three-component formation fluids from an oil well. Thus, more specifically, the invention provides a method of distinguishing between the gas, water and oil components of a three-phase oil well formation fluid, in which method:

there is inserted into the fluid a closely-spaced pair of optical probes of the invention one having a tip angled to cause total internal reflection when in gas but not when in water or oil and the other having a tip angled to cause total internal reflection when in gas or water but not when in oil;

there is measured the light returned by the probes, to give an indication of whether or not each probe is in a component which for that probe causes total internal reflection;

and these binary indications are logically combined to indicate in which component the probes are disposed.

The invention also provides apparatus for use in a method of distinguishing between the components of a multiphase fluid, especially the gas, water and oil components of a three-phase oil well formation fluid, which components have significantly different refractive indices, which apparatus comprises:

a closely-spaced set of optical probes of the invention having tips "matched" to—with different interface/normal angles θ, each angle θ being set between the critical angles for—a phase pair of interest, especially a closely-spaced pair of optical probes one having a tip angled to cause total internal reflection when in gas but not when in water or oil and the other having a tip angled to cause total internal reflection when in gas or water but not when in oil;

light source and detector means for launching light into the probes, and means for measuring the light returned by the probes, to give an indication of whether each probe is in a component which causes total internal reflection or not;

and computational means for logically combining these binary indications to indicate in which component the probes are disposed.

The invention provides a method of distinguishing between the components of a multiphase fluid which components have significantly different refractive indices. It will be evident that if the refractive indices of the two components are very close together it may be rather difficult to distinguish between the two with reliability, because the uncontrollable variables, such as the exact probe tip angle, may make it hard to be confident as to which component is giving which effect. To have confidence in the results the components' indices should preferably be well spaced—as is typically the case with gas (1.0), water (1.3) and oil (1.5) (though it should be remembered that in a fluid such as an oil well formation fluid the actual values experienced may be rather different). In a laboratory situation it might be possible consistently to distinguish between components the refractive indices of which are less than 0.05 apart, whereas on an oil rig this might present some difficulty.

Although the method of the invention is as stated above particularly applicable to use with the two- or three-phase gas (methane), water (brine) and oil fluid encountered in an oil well—and was indeed invented for that purpose—it may be of value with all sorts of fluids, and not just those found in oil wells. For example, in the biological/biochemical fields it might be employed to discriminate between specimens of differing refractive index of fluids such as blood (moving in a blood vessel) or some body fluid sample (e.g., a urine sample). The method of the invention wherein probes are used to distinguish the components of a fluid involves the insertion into the fluid under examination of a set of optical probes—that is to say, it places the tips of the probes within and immersed in the fluid, so the tips are bathed therein and have fluid actually in contact therewith. The mechanism to achieve this immersion may be any found convenient; in an oil well context, for example, the probes could be in a tool lowered down the well bore to the position of interest, or in some sort of metering device positioned at the wellhead (at the surface, where any gas in the fluid will have expanded, as the fluid comes up to the surface, and the ambient pressure drops, until it constitutes perhaps as much as 90% or more by volume of the fluid). In either case the mechanism will in effect be a mounting past which formation fluid can flow and from which the probes project into the passing fluid. The probes will usually be positioned with their long axis parallel to the fluid flow and their tips facing the oncoming fluid, although other orientations are possible.

Although, as is discussed in more detail hereinafter, the invention recommends a novel design of optical probe especially suited for the purpose, in general principle the probes in the set may, apart from their doubly-reflective tip design, be of any convenient type. They may thus have cores which may be either single- or multimode and of either stepped- or graded-index optical fibre. Accordingly, in a general sense the probes need no detailed discussion at this time. Nevertheless it may be helpful to observe that a typical probe is a silica glass optical waveguide of around 50 micrometer diameter forming the core of a 125 micrometer fibre made by cladding the core with a germania-doped silica layer (which may itself be clad with a hard polymer protective layer to give a 150 micrometer fibre), the whole mounted with a resin glue into a steel needle of external diameter 315 micrometer. A probe of this type might thus be made from some 50/125-E4008A-R fibre (available from Optical Fibres, of Deeside, Clwyd) mounted in a Coopers #29 needle.

It will also be useful to observe that, in the case of a probe with a tip so shaped that the cladding exterior surface takes part in the re-reflection of the TIRed light, the probe tip will (as has been alluded to hereinbefore) bear immediately around the outside of the cladding a highly reflective coating. This coating can typically be of silver or some other metal, or combination of metals, such as gold, platinum, nickel, aluminium, molybdenum and/or chromium (although as will be appreciated it is possible to employ instead a multilayer dielectric coating that provides near 100% reflection using interference effects), to assist in returning into the core, by simple reflection, the light reflected back from the tip, and thus to ensure that this light is sent back up the core to the detector.

The individual probes in the set of probes are closely-spaced one to another. As will be clear, this close spacing is because they need to have their tips immersed effectively in the same portion of the fluid—in an oil-well formation fluid of, say, bubbles of gas and water dispersed in a continuous oil phase the probe set tips should all be in the same gas or water bubble, or should all be in the oil phase. In this context, then, "closely spaced" generally means as close as possible, and though, to reduce problems with static wetting fluid lodging in concave parts of the combination, it is desirable to have the tips some small distance apart—say, 0.5 mm—it is notionally possible for the individual probes actually to touch their neighbours. Where there are two or more touching individual probes the touching combination makes a "double" or "multiple" probe (and in a special case where two such probes are disposed with their major tip surfaces generally co-planar the two make a whole referred to hereinafter as a "twin" probe). In such a case, a dual (or twin) probe made using #29 needles, as mentioned above, would be a mere 660 micrometer, or 0.66 millimeter, across. Even smaller probe sets can be made if the several individual probes are placed within a single protective needle.

The probes in the set have differently-angled tips matched to the different critical angles for the probe/phase pairs of interest. More particularly, in the case of a probe pair for distinguishing between the components of a three-phase gas/water/oil formation fluid, one probe has a tip angled to cause total internal reflection when in gas but not when in water or oil and the other has a tip angled to cause total internal reflection when in gas or water but not when in oil. Naturally, the actual angles chosen will depend upon the refractive indices (and thus the several probe/component critical angles) of the probe and of the fluid components, or sets of components, to be distinguished, and it is believed to be within the competence of the Reader to determine for any particular set of fluid components those indices (either by looking them up or by measuring them) and then to select the angles and combinations of angles necessary. By way of illustration, for the two-probe investigation of the particular three phase oil well formation fluid mentioned above—methane gas ($n=1.0$), water/brine ($n=1.33$) and oil ($n=1.5$) —using a silica glass probe ($n=1.46$), appropriate probe angles $\alpha$ are 45° and 17° (providing light/interface normal angles $\theta$ of 45° and 73° respectively). Some further guidance on the angles to be used for a silica fibre probe may be derived from a graph of the tip/water interface as a function of water (brine) refractive index discussed hereinafter with reference to the accompany Drawings.

Hereinbefore the probe tip's interface surface has been implied to be planar—that is, flat. However, although a planar surface is preferred, not least because is simplifies an understanding of the optics of the device, in practice it has been found that a degree of curvature, perhaps giving the surface a part-conical form, is not unacceptable, and may even be beneficial in order to give some small focusing effect that will assist in returning the reflected light back into the core.

In carrying out the method of the invention light is generated and input to each probe, to be transmitted along the probe core to the tip, and the light reflected at the tip, and thus returned by the probe back along its core, is detected and measured to give an indication of whether that probe is in a fluid component which causes total internal reflection or not. In broad outline, then, the working of each individual probe is perfectly conventional, as is the light generating, inputting, detecting and measuring apparatus, and needs no detailed discussion at this time. Nevertheless it may be useful to observe that in practice a convenient source of light is an infrared-light-emitting diode (typically a Honeywell HFE4050 emitting non-coherent infrared at about 850 nm) or laser (such as a BT&D LST0605-FC-A emitting at 1,300 nm), and that the light may, if the fibre is of a suitable type appropriately rotationally aligned, optionally be polarised to assist in optimising the medium discrimination. The light is injected, via a beam splitter or optical fibre coupler, into the probe's fibre, and is transmitted therealong down to the tip. At the tip either there is or there is not total internal reflection, depending upon in which fluid component the tip is immersed at the time, and thus either a lot or only a very little light is returned back along the fibre, and is directed to the detector (rather than back to the source) by the beam splitter or coupler. This returned light is then detected (a Honeywell HFD3022 photodiode is suitable for the LED source identified above, while a BT&D PDT0X1X photodiode is suitable for the laser) and measured, to provide the desired indication of the component's reflective capability.

What is, perhaps, a key feature of the preferred method of the invention is the use of the light returned by the probes in a set of probes to give an indication of whether each probe is in a component which causes total internal reflection or not, and then logically to combine these binary indications to indicate in which component the probes are disposed. With the benefit of hindsight this might seem to be so simple as to be obvious, and yet it has not hitherto been proposed, despite all the known problems associated with using optical probes to distinguish fluid components one from another. For a gas/water/oil oil well formation fluid investigated with only two probes this logical combination is easy: as noted hereinbefore, if both probes have a high output the phase is gas, if one is high but the other is low it's water, and if both probes are low it's oil. The application of this principle to other situations, where there are used probes with critical angles spread over a range corresponding to the components of the multiphase fluid being measured, is more complex in practice even if it is still fairly simple in theory, but even so it will be easily appreciated, and so needs no detailed explanation at this time.

The actual technique by which the results are logically combined to indicate in which phase the probes are presently immersed may be any convenient, and needs no detailed discussion here. Even so, it will probably be helpful to note that simple electronic apparatus, containing suitable AND and OR gates, to achieve this sort of logical analysis is very well known, and the task could of course even be entrusted to a conventional desk-top computer suitably programmed.

Although, as has been observed hereinbefore, in general principle the set of probes employed in the method of the invention may be of any convenient type, save for their having differently-angled tips matched to the different critical angles for the probe/phase pairs of interest, in fact the invention provides a novel design of optical probe pair especially suited for the purpose. More specifically, the invention provides the idea of the double probe, being two individual probes—two separate clad and coated optical fibre cores—disposed immediately adjacent each other. The individual probes in the pair of probes may be identical, and for convenience be disposed with their major angled tip surfaces substantially co-planar, in which case the pair is a twin probe (both components providing the same output data, but one staggered in space, and thus—in use—in time, from the other), or, alternatively, the individual probes may have differently-angled tips matched to the different critical angles for the probe/phase pairs of interest, and especially one probe having a tip angled to cause total internal reflection when in gas but not when in water or oil and the other having a tip angled to cause total internal reflection when in gas or water but not when in oil, in which case the pair is a dual probe.

The twin or dual probes of the invention are almost literally two individual probes mounted together (although possibly the two optical fibres can be mounted in a common protective needle rather than each being in a separate needle). What is said herein for the individual probes when actually separate applies equally to the probes when mounted together as a twin, and needs no further comment here.

The method and apparatus of the invention actually provides an indication of the nature of the fluid component into which the probes at a chosen observation point extend at any given time. By averaging over time, this yields an estimate of the average volume fractions of the pipe or other duct which are occupied by the several phases. These volume fractions are themselves valuable data in flow measurements on multiphase fluids.

One use of a twin probe would be to determine velocities of "bubble" interfaces from the time delays between corresponding transitions observed in the signals derived from the two individual probes making up the twin.

A surface flow measurement apparatus or a downhole flow logging tool made using a probe—and especially the apparatus and method—of the invention is of a simple design, and relatively inexpensive to manufacture. Although primarily for surface operation, the tool can be given a robust construction capable of withstanding the hostile environmental conditions encountered downhole, and is usable as a continuous logging device, being logged up and down the well, whilst making detailed volume fraction and velocity estimates for each fluid component.

BRIEF DESCRIPTION OF THE DRAWINGS

Various embodiments of the invention are now described, though by way of illustration only, with reference to the accompanying diagrammatic Drawings (which are not to scale) in which.

DESCRIPTION OF THE PREFERRED EMBODIMENTS

Figure 1:
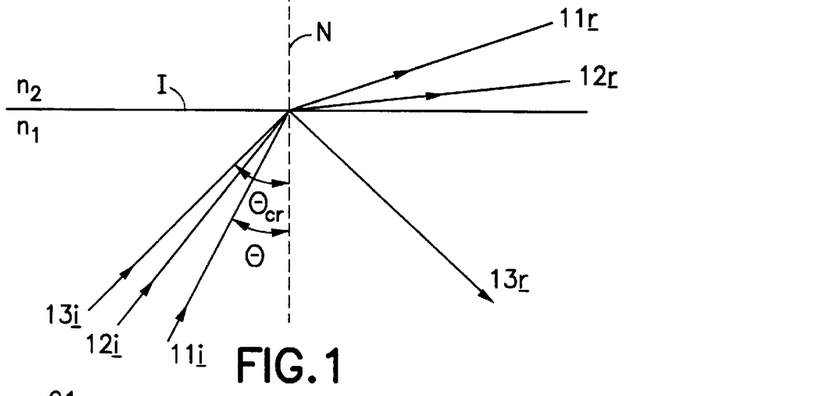
FIG. 1 illustrates the concept of total internal reflection at an interface.

The concept of total internal reflection is illustrated in FIG. 1. A ray of light ($11_i$) that is directed towards and thus incident upon the interface I between two transparent media (such as water and air) one of which (the bottom one as viewed, perhaps water) has a refractive index $n_1$ that is greater than the refractive index $n_2$ of the other (the top one as viewed, perhaps air) can pass from the bottom to the top medium through the interface, being refracted (bent) as it goes on to become the refracted ray ($11r$), provided the angle θ the incident ray $11i$ makes with the line N normal to the interface is less than the critical angle $θ_{cr}$. As the angle θ made by the incident ray gets larger, the refracted ray gets closer to the interface—thus, ray $12i$ is refracted as $12r$. Eventually, the incident ray angle becomes only infinitesimally greater than the incident angle, whereupon the refracted ray can be imagined as being actually in the interface surface (this is not shown)—and with the next increase in the incident ray angle the light ($13i$) is no longer refracted at all, but is totally reflected internally of the bottom medium instead, to give ray $13r$.

Figure 2:
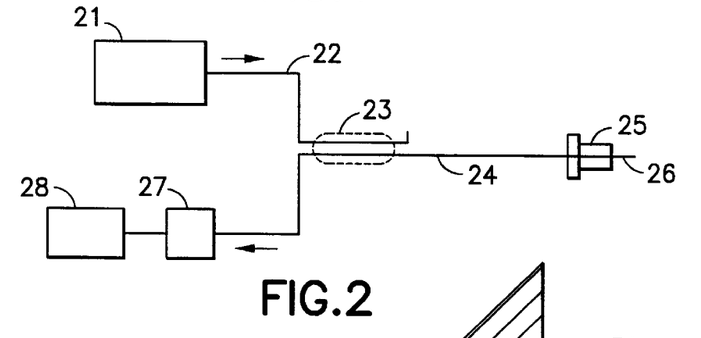
FIG. 2 shows schematically the idea of a fibre optic probe.

This principle is behind both the idea of optical fibres per se and the idea of the present invention using angled tip probes. The overall probe system is shown in FIG. 2. A light source (21) outputs light into a short length of optical fibre (22) whence it passes into a coupler (23) in which it is allowed to "leak" into another optical fibre (24). This second fibre 24 terminates in a probe (25) with an angle-ended tip (26: shown considerably enlarged; details of the actual tip end can be seen in FIGS. 3A et al) that in use is placed in the fluid under examination.

Light travelling down the probe's fibre 24 to the tip 26 will, according to the invention, be totally internally reflected at the tip depending on the refractive index of the medium in which it is positioned. This reflected light then travels back up the fibre 24, through the coupler 23, and on to a photodetector (27) the output of which is fed to a logic system (28) which itself outputs (not shown) the desired indication identifying nature of the fluid being examined.

Details of a number of probe tips are shown in FIGS. 3, 4 and 5 (FIG. 3F shows the first form of probe of the invention, wherein TIRed light is reflected from the secondary reflection surface straight back up the core of a wide-core fibre, while the other Figures show examples of the second form, wherein reflection back is via the interface).

In FIG. 3A is shown the basic angled tip (generally 31). The probe has a thin fibre optic core (32) within a wider cladding (33) itself coated on its outer surface by a reflective coating (34; this is very thin, and is shown merely as a thick black line). Using a resin "glue" (35) the clad fibre is mounted within a hollow protective steel needle (36).

The very end of the tip—the surface (37) that will be the interface with the surrounding fluid into which the probe is placed—is cut off (and smoothed as optically flat as possible) at an angle α (the angle the plane of the tip, and thus of the interface, makes with the axis of the probe; in FIG. 3A this angle is 45°). If, then, light travels down the fibre 32 to the interface 37 it arrives there making an angle θ of 90–α to the normal N (in this case, also 45°); if this angle θ is greater than the critical angle $θ_{cr}$ for the media combination of the fibre material and the fluid currently at the interface then the light is not transmitted through the interface but is instead totally internally reflected (in the manner shown in FIG. 1) to give a ray Lr. This ray impinges on the claddings reflective coating 34, and is there reflected straight back to the interface where it is reflected again, straight back up the fibre 32 to the waiting detector (27 in FIG. 2).

FIGS. 3B and 3C show differently shaped and angled probe tips useful in the invention. In that of FIG. 3B the tip's main interface surface 37 has been cut at a particularly oblique angle (α is about 20°) while a secondary surface, or facet (38), has been formed by cutting across the "point" of the probe at an angle β to the fibre axis (actually, angle β is between an extension of the surface 28 and an extension of the axis). This secondary surface carried the reflective coating 34, and to ensure that light that is totally internally reflected (along Lr) as it exits the tip of the fibre 32 is indeed re-reflected by the reflective coating 34 back along the same path it is necessary to arrange that the relationship between α and β be such that $$\sin\beta = \frac{n_{core}}{n_{clad}} \times \sin(90° - 2\alpha)$$

(where n is the relevant refractive index).

Unlike the FIG. 3B tip, where the core/cladding material is necessarily rather exposed to the passing fluid, in the embodiment of FIG. 3C the very end of the tip is the needle itself, so the tip is possibly better protected from the fluid.

The FIG. 3C version is very like that of FIG. 3B, even though at first sight it looks quite different. In the 3C case both the second surface 38, at a large angle β to the fibre axis, and the cladding 33 have a reflective coating 34, and the path of light Lr totally internally reflected from the main interface surface 37 involves reflection twice, first off the cladding's coating and then off the second surface's coating (and then back along the same route to the fibre, to be guided back therealong to the detector).

The probe tip shown in FIG. 3D is much like that of FIG. 3B save that, instead of a fine-core single-mode stepped index fibre it employs a wider-core multi-mode fibre (39), this enabling greater angular tolerances during manufacture.

FIG. 3E shows a corner-reflector version of the type of FIG. 3A but with a wide-core fibre. Instead of the single simple reflective surface of the FIG. 3A embodiment this version has a corner reflector made of two reflective surfaces 34a and 34b meeting at rightangles (the second one, 34b, is the outer surface of the fibre). Light travelling down the fibre towards the interface 37 along ray A, for example, is reflected off the interface (when TIR occurs) towards reflective surface 34b, off that surface towards reflective surface 34a, off that surface back towards the interface 37 (this part of its path is, because of the rightangle in the corner reflector, parallel to that from interface to surface 34b), and finally off that surface back up the fibre along path B.

FIG. 3F shows a wide-core multi-mode fibre, its tip faceted (to make two plain surfaces 37,38 at rightangles to one another) to constitute a probe of the first form—that is, one wherein the TIRed light is reflected by the secondary reflection surface straight back up the fibre. Light guided down the fibre core 39 reaches the tip and is reflected off either the interface 37 or the secondary reflective surface 38, and is then re-reflected by the other of these two back up the fibre core 39 (obviously, it is immaterial whether the light reaches the interface before the secondary reflective surface or after, the effect is the same). Provided that the included angle between the interface 37 and the secondary reflective surface 38 is a rightangle then TIRed light will always be reflected straight back up the fibre, regardless of the angle α the interface surface makes with the fibre axis.

Figure 3G:
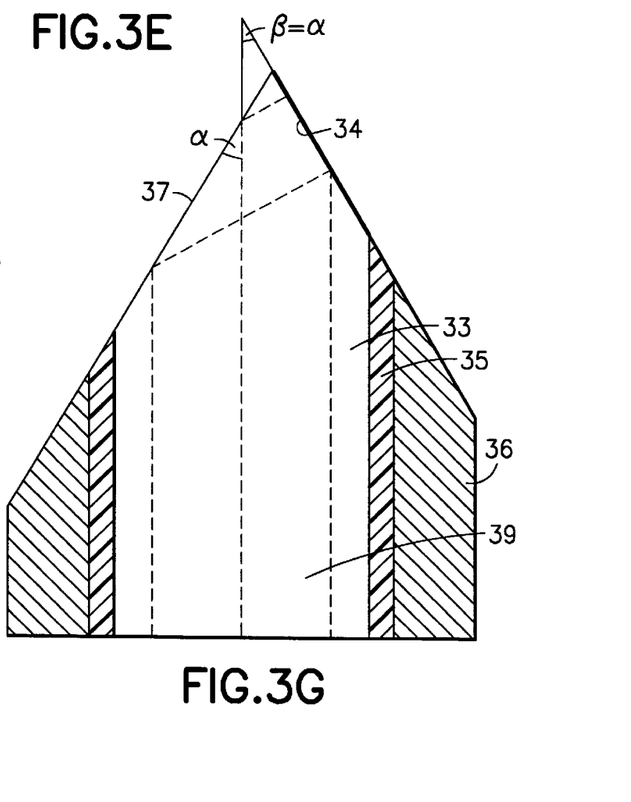

FIG. 3G shows a version of the fibre tip of the invention wherein the geometry of the tip is such that light reaching an acute-angled secondary reflective surfac 34 does not pass through the cladding 33, so that the relationship between α and β is β=90°–2α. The Figure also shows a version with a tip that is symmetrically angled—α=β—but asymmetrically positioned—as can clearly be seen, the tip is off-axis (in this Figure it is shown displaced across to the right as viewed). It will be evident, from the geometry of the situation, that in this special case of angular symmetry α must be 30°.

Figure 4A:
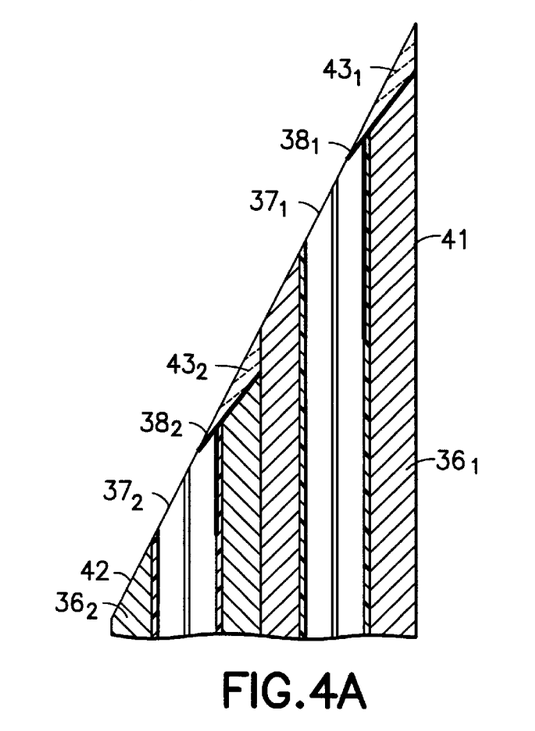
FIGS. 4A & B show schematically the nature of two different "double" probe tips for use in the method of the invention.
Figure 4B:
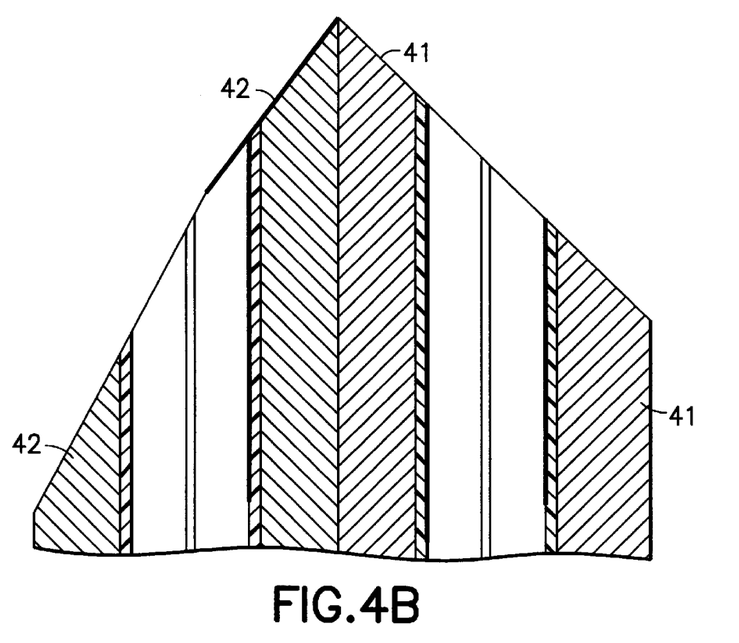

FIGS. 4A and 4B show different forms of paired probes in accordance with the invention. In FIG. 4A there is shown what is referred to as a twin probe, which consists of two individual identical probe needles (41,42) each like that probe tip shown in FIG. 3C. The two individual core/cladding-containing needles (361,362) are actually touching, front to back, with the two tip interface surfaces (371,372) essentially co-planar (and in each case the space left by the angled subsidiary surfaces 381,382) is filled by a fillet of resin 431,432) to provide overall a slightly convex surface. If the twin probe is positioned with this smooth surface aligned with the flow direction of the fluid under examination, then as the fluid flows smoothly past the two tips, from one to the other, it is easy to use the outputs from the two probes to provide fluid flow speed information. As can be appreciated, similar twin probes can be made using individual probes like those shown in FIGS. 3A, 3B and 3D The pair of probes shown in FIG. 4B is what is referred to as a dual probe, which in this case consists of two individual differently-shaped probe needles 41,42 one of them (41) like that of FIG. 3A, the other (42) like that of FIG. 3C. Here, the two individual needles 361,362 are back to back.

Figure 5A:
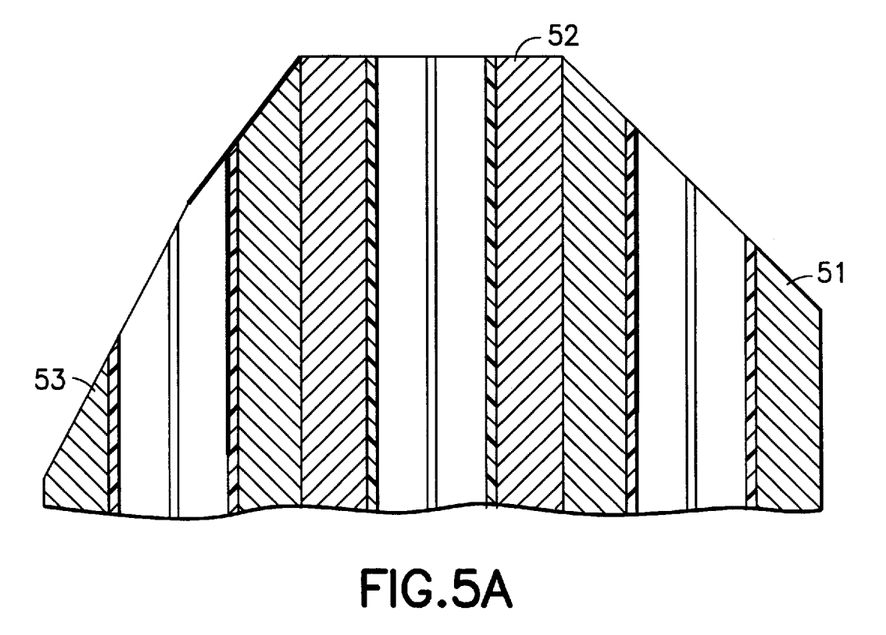
FIGS. 5A & B show schematically the nature of a three-component probe tip for use in the method of the invention.
Figure 5B:
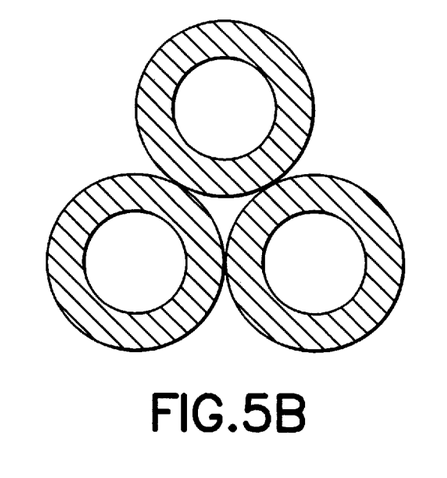

In FIGS. 5A and 5B there are shown two views of a three-needle probe. FIG. 5A shows the three individual needles (51,52,53) as though they were arranged side by side (though in reality a cluster like that of the "sectional" view of FIG. 5B is most likely). One needle (51) is like that of FIG. 3A, and one (53) like that of FIG. 3C; the "middle" needle is like one of those "right" probe needles presently employed (and referred to hereinbefore). A probe of this type could be employed for bubble interface velocity measurements by interferometric methods.

Figure 6A:
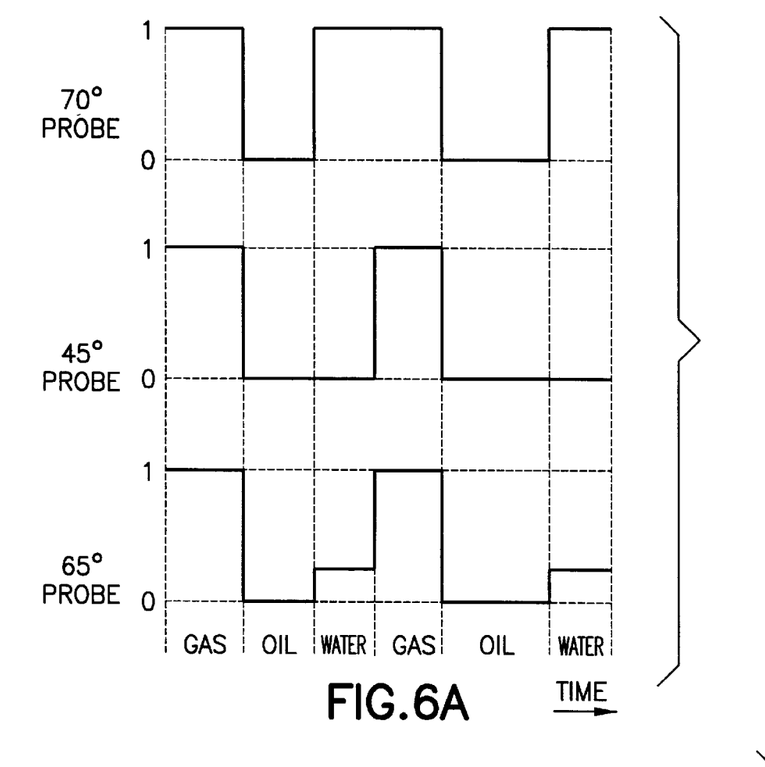
FIGS. 6A & B show schematically various probe outputs obtained using the method of the invention.

When a probe is placed in a flowing three-phase fluid, as typified by a oil well drill-pipe conducting gas, oil and brine, the probe tip is going to be in contact with each fluid phase at different moments. The sort of probe outputs that can then be expected when using a respectively 70°, 45° and 65° are shown in FIG. 6A. The signal levels change as the different fluid phases pass by the tips, and it will be clear that discrimination of the three phases one from the other can be achieved by performing a simple binary arithmetic logic operation on the 75° and 45° tip outputs (or by setting thresholds for the 65° tip outputs).

Figure 6B:
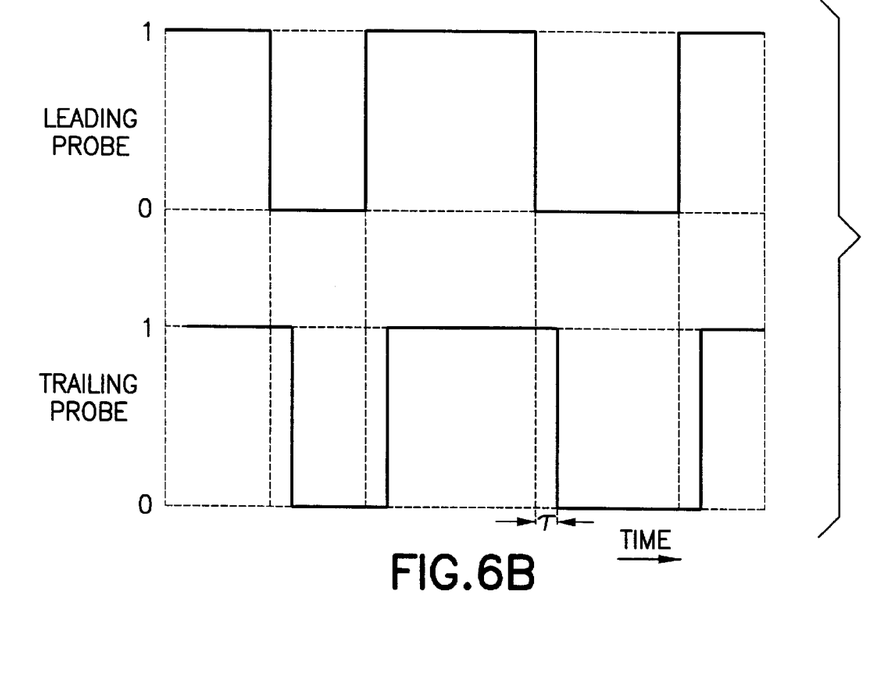

FIG. 6B shows the signals from a twin probe installation like that of FIG. 4A. The "time of flight" τ can be used to calculate the speed of a given fluid phase (which depends, of course, on the exact angle of the probes' main interface surface with the flow direction).

Figure 7:
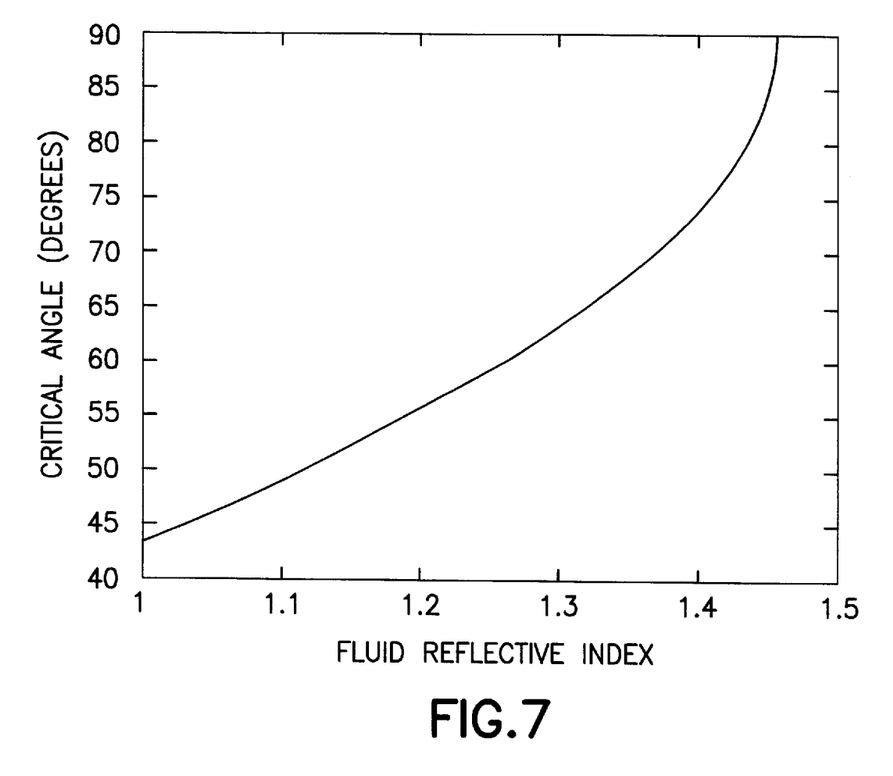
FIG. 7 shows for a silica fibre a graph of probe tip/fluid critical angle against fluid refractive index In all of FIGS. 3 and 4 the probe tips are viewed as diametral surfaces in a plane normal to the tip surfaces.

Finally, FIG. 7 shows a graphical plot of refractive index against critical angles $\theta_{cr}$ (using a silica fibre of index n=1.46). This may be used to assist in the choosing of angles α to discriminate between particular pairs of fluids.

We claim:

1. An optical fibre probe which includes a fibre tip having at least one planar surface at an angle α to the fibre axis as a fluid-sensitive interface and at least one other surface at a different angle β to the fibre axis and forming part of an intrinsically highly-reflective secondary reflector, the two surfaces being asymmetrically oriented with respect to the fibre axis and being so oriented both mutually and with respect to the fibre axis that light guided along the fibre to the tip and reflected off the fluid-sensitive interface surface towards the secondary reflector is reflected back along the fibre, characterized in that the secondary reflector is a corner reflector including two reflective surfaces.

2. A probe as claimed in claim 1, wherein the secondary reflector is made of two reflective surfaces meeting at a right angle.

3. A probe as claimed in claim 1, wherein one of the reflective surfaces of the secondary reflector is the outer surface of the fibre.

4. A probe as claimed in claim 1, wherein the angle α is chosen so as to distinguish gas from liquid or oil and other fluids.

5. A probe as claimed in claim 4, wherein the fibre is made of a silica glass and the angle α is chosen so as to provide a light/interface normal angle θ of just fractionally below the probe/water critical angle.

6. A probe as claimed in claim 4, wherein, for distinguishing gas from liquid, the angle α is within the range of 25 degrees to 45 degrees, while for distinguishing oil from water/brine or gas, the angle α is in the range of 5 degrees to 25 degrees.

7. A probe as claimed in claim 1, wherein the fluid sensitive interface of the fibre is provided with a layer, said layer not causing Total Internal Reflection at its interfaces with the fibre material, and is not wet by any of the fluid components likely to be encountered.

8. A probe as claimed in claim 1, wherein the fluid sensitive interface of the fibre is provided with a layer, said layer not causing Total Internal Reflection at its interface with the fibre material, and is only wet by such a component the refractive index of which is of a value relative to that of the probe's fibre such that no total internal reflection is expected to occur when the tip is immersed in that component.

9. A probe as claimed in claim 8, wherein the layer is made of a hard, protective material.

10. A probe as claimed in claim 9, wherein the hard, protective coating material is diamond or Diamond-Like Carbon, or partially-hydrogenated or partially-fluorinated variant thereof, optionally with a proportion of silicon.

11. A probe as claimed in claim 1, further comprising a light source to launch light into the fibre, a detector to detect light traveling back after reflection at the tip of the fibre, and a logic system to give indication of the nature of the fluid being examined.

12. Two probes as claimed in claim 1, arranged as double probe.

13. A double probe as claimed in claim 12, wherein either the individual probes in the pair of probes are identical, and are disposed with their major angled tip surfaces substantially co-planar, or, alternatively, the individual probes have differently-angled tips matched to the different critical angles for the probe/phase pairs of interest.

14. A double probe as claimed in claim 13, wherein the individual probe optical fibres are mounted in a common protective needle.

15. A probe as claimed in claim 12, further comprising a light source to launch light into the fibres, a detector to detect light traveling back after reflection at the tip of the fibres, and a logic system to give an indication of the nature of the fluid being examined.

16. A borehole measurement tool including at least one probe having at least one planar surface at an angle α to the fibre axis as a fluid-sensitive interface and at least one other surface at a different angle β to the fibre axis and forming part of a corner reflector, the two surfaces being asymmetrically oriented with respect to the fibre axis and being so oriented both mutually and with respect to the fibre axis that light guided along the fibre to the tip and reflected off the fluid-sensitive interface surface towards the secondary reflector is reflected back along the fibre.

17. An optical fibre probe which includes a fibre tip having at least one planar surface at an angle α to the fibre axis as a fluid-sensitive interface and at least one other surface at a different angle β to the fibre axis and providing, or forming part of, an intrinsically highly-reflective secondary reflector, the two surfaces being asymmetrically oriented with respect to the fibre axis and being so oriented both mutually and with respect to the fibre axis that light guided along the fibre to the tip and reflected off the fluid-sensitive interface surface towards the secondary reflector is reflected back along the fibre, characterized in that the fluid-sensitive interface is provided with a layer not causing Total Internal Reflection at its interface with the fibre material, and being only wet by a component, the refractive index of which is of a value relative to that of the probe's fibre such that no Total Internal Reflection is expected to occur when the tip is immersed in that component.

18. A probe as claimed in claim 17, wherein the layer is made of a hard, protective material.

19. A probe as claimed in claim 17, wherein the hard, protective coating material is diamond or Diamond-Like Carbon, or a partially-hydrogenated or partially-fluorinated variant thereof, optionally with a proportion of silicon.

20. A method of distinguishing between the components of a multiphase fluid, comprising:

inserting into said fluid an optical fibre probe having at least one planar surface at an angle α to the fibre axis as a fluid-sensitive interface and at least one other surface at a different angle β to the fibre axis and forming part of a corner reflector, the two surfaces being asymmetrically oriented with respect to the fibre axis and being so oriented both mutually and with respect to the fibre axis that light guided along the fibre to the tip and reflected off the fluid-sensitive interface surface towards the secondary reflector is reflected back along the fibre;

activating a light source to launch light into said fibre probe;

measuring light returned by the probe, to give an indication of whether the probe is in a fluid component which causes Total Internal Reflection or not; and using this indication to indicate in which fluid component the probe is disposed.

21. A method as claimed in claim 20, wherein the multiphase fluid is a fluid from a subterranean formation.

22. A method as claimed in claim 20, wherein the components of the multiphase fluid have significantly different refractive indices, and the inserted probe comprises a closely-spaced set of two optical fibres having differently-angled tips matched to the different critical angles for the probe/component pairs of interest, and the indications are combined to indicate in which component the probes are disposed.

23. A method, as claimed in claim 22, wherein one fibre has a tip angled to cause Total Internal Reflection when in gas but not when in water or oil and the other has a tip angled to cause Total Internal Reflection when in gas or water but not when in oil.

24. A method as claimed in claim 22, wherein the spacing of the individual fibres in the set thereof is such that each actually touches its neighbours.

* * * * *